United States Patent [19]

Schade et al.

[11] Patent Number: 4,879,310

[45] Date of Patent: Nov. 7, 1989

[54] NEW CYANOHYDRIN IODOPROPARGYL ETHERS, PROCESS FOR THEIR PREPARATION AND THEIR USE AS MICROBICIDES

[75] Inventors: Gerold Schade, Cologne; Wilfried Paulus; Hans-Georg Schmitt, both of Krefeld, all of Fed. Rep. of Germany

[73] Assignee: Bayer Aktiengesellschaft, Leverkusen, Fed. Rep. of Germany

[21] Appl. No.: 189,580

[22] Filed: May 3, 1988

[30] Foreign Application Priority Data

May 19, 1987 [DE] Fed. Rep. of Germany ....... 3716682

[51] Int. Cl.$^4$ ................. C07C 121/30; C07C 121/48; A01N 37/34
[52] U.S. Cl. .................................. 514/519; 514/526; 558/303; 558/430; 558/432; 558/449
[58] Field of Search ............... 558/430, 432, 303, 449; 514/519, 526

[56] References Cited

U.S. PATENT DOCUMENTS 4,322,442  3/1982  Jager et al. ..................... 514/526 X
4,686,236  8/1987  Schade et al. .................. 558/449 X

OTHER PUBLICATIONS

Weygand/Hilgetag; "Preparative Organic Chemistry", (1972), pp. 159–161, John Wiley & Sons, N.Y., London, Sydney, Toronto.

Primary Examiner—Joseph Paul Brust
Attorney, Agent, or Firm—Sprung Horn Kramer & Woods

[57] ABSTRACT

The invention relates to new cyanonhydrin iodopropargyl ethers of the formula

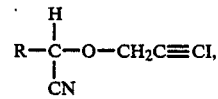

in which
R denotes $C_1$–$C_{10}$-alkyl, $C_2$–$C_{10}$-alkenyl, $C_{5}$–$C_{8}$-cycloalkyl or -cycloalkenyl, which can be optionally substituted by $C_1$–$C_4$-alkyl or halogen, a process for their preparation and their use as microbicides for the preservation of industrial materials.

3 Claims, No Drawings

NEW CYANOHYDRIN IODOPROPARGYL ETHERS, PROCESS FOR THEIR PREPARATION AND THEIR USE AS MICROBICIDES

The invention relates to new cyanohydrin iodopropargyl ethers, a process for their preparation and their use as microbicides in the preservation of materials.

Iodopropargyl ethers which have antimicrobial properties are already known (see, for example, DE-OS (German Published Specification) 3,224,503 and 3,526,789). However, the microbicidal properties of these known compounds are inadequate for numerous fields of application. Thus, for example, the iodopropargyl ethers described in DE-OS (German Published Specification) 3,224,503 have sufficient activity only against certain harmful microbes. Although the iodopropargyl ether described in DE-OS (German Published Specification) 3,526,789 has a good microbicidal activity, it is nevertheless unsuitable as a microbicide for industrial materials, especially in paints, since it does not have the resistance to leaching required for this intended use.

It has now been found that iodopropargyl ethers which are derived from certain cyanohydrins have an improved microbicidal action in comparison with the already known iodopropargyl ethers, have an increased action spectrum, and also have the high resistance to leaching required for use in paints.

The invention thus relates to new cyanohydrin iodopropargyl ethers of the formula

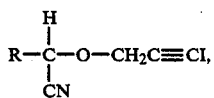

in which
R denotes $C_1-C_{10}$-alkyl, $C_2-C_{10}$-alkenyl, $C_5-C_8$-cycloalkyl or cyclo-alkenyl, which can be optionally substituted by $C_1-C_4$-alkyl or halogen.

Preferred alkyl radicals are those with 2 to 7 carbon atoms, preferred alkenyl radicals are those with 2 to 5 carbon atoms, preferred cycloalkyl radicals are those with 6 or 7 carbon atoms and preferred cycloalkenyl radicals are those with 6 or 7 carbon atoms, it being possible for the cycloalkyl and cycloalkenyl radicals to be optionally substituted by methyl, ethyl, propyl, chlorine or bromine. Examples which may be mentioned are: ethyl, propyl, isopropyl, butyl, tert.-butyl, 1-ethylpentyl, cyclohexyl, methylcyclohexyl, cyclohexenyl, and methyl-cyclohexenyl, preferably ethyl, propyl, and cyclohexenyl and especially preferably cyclohexenyl.

The invention furthermore relates to a process for the preparation of the cyanohydrin iodopropargyl ethers of the formula

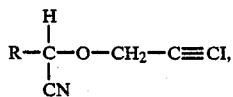

in which
R denotes $C_1-C_{10}$-alkyl, $C_2-C_{10}$-alkenyl, $C_5-C_8$-cycloalkyl or -cycloalkenyl, which can be optionally substituted by $C_1-C_4$-alkyl or halogen, which is characterized in that cyanohydrin propargyl ethers of the formula II

in which
R has the abovementioned meaning, are reacted with iodinating agents in the presence of solvents and/or diluents and in the presence of bases at temperatures of $-10°$ C. to $+30°$ C.

Iodinating agents which can be used in the process according to the invention are iodine and/or compounds which supply iodide ions, such as sodium iodide and ammonium iodide, in the presence of oxidizing agents, such as sodium hypochlorite, calcium hypochlorite and/or hydrogen peroxide.

Suitable bases are both inorganic and organic bases, such as sodium hydroxide, calcium hydroxide, sodium methylate, potassium tert.-butylate and/or sodium isobutylate, preferably sodium hydroxide and/or sodium methylate.

Suitable solvents for the process according to the invention are, for example, water or alcohols, such as methanol and ethanol, or mixtures thereof.

The iodination is preferably carried out at temperatures from $-5°$ C. to $+20°$ C.

According to the invention, about 1 mol of propargyl ether of the formula II is used with about 1.0 to 1.5 mol of iodinating agent, preferably 1.0 to 1.2 mol of iodinating agent.

The most favourable amounts of bases and of solvents and/or diluents can in each case easily be determined by preliminary experiments. About 1 to 5, preferably 1.2 to 3 mol of base per mol of propargyl ether of the general formula II and the same to five times, preferably two or three times, the amount by weight of solvent and/or diluent are usually employed.

The propargyl ethers of the general formula II are known in some cases (Synth. Commun. 7 (4), 273–281 (1977)). They can be obtained by reacting cyanohydrins of the general formula

with propargyl halides in the presence of bases. It may be advantageous here not to isolate the cyanohydrins III but merely to prepare them in situ and to further react them immediately with the propargyl halide (analogously to Can. J. Chem. 55, 4200 (1977)).

The new cyanohydrin iodopropargyl ethers according to the invention can be used as active compounds for combating microorganisms on plants, but in particular in industrial materials which can be decomposed by microorganisms.

According to the invention, industrial materials are non-living materials which have been treated for use in industry. Technical materials which are to be preserved by the active compounds according to the invention against microbial change or destruction are, for example, adhesives, sizes, paper and card, textiles, leather, wood, paints and plastics articles, cooling lubricants and other materials which can be infested or decomposed by microorganisms. Parts of production lines, for example cooling water circulation systems, which can be impaired by multiplication of microorganisms may also be mentioned in the context of the materials to be preserved. Industrial materials which may be mentioned as preferred in the context of the present invention are adhesives, sizes, paper and card, leather, wood, paints, cooling lubricants and heat transfer liquids.

Examples which may be mentioned of microorganisms which can cause degradation of or a change in the industrial materials are bacteria, fungi, yeasts, algae and slime organisms. The active compounds according to the invention preferably act against fungi, in particular moulds, fungi which discolour and destroy wood (Basidiomycetes) and phytopathogenic fungi and against slime organisms and algae.

Microorganisms of the following genera may be mentioned as examples: Alternaria, such as *Alternaria tenuis*, Aspergillus, such as *Aspergillus niger*, Botrytis, such as *Botrytis cinera*, Chaetomium, such as *Chaetomium globosum*, Coniophora, such as *Coniophora puteana*, Lentinus, such as *Lentinus tigrinus*, Penicillium, such as *Penicillium glaucum*, Piricularia, such as *Piricularia oryzae*, Polyporus, such as *Polyporus versicolor*, Aureobasidium, such as *Aureobasidium pullulans*, Sclerophoma, such as *Sclerophoma pityophila*, Trichoderma, such as *trichoderma viride*, Escherichia, such as *Escherichia coli*, Pseudomonas, such as *pseudomonas aeruginosa* and Staphylococcus, such as *Staphylococcus aureus*.

An acitve compound according to the invention can be converted into the customary formulations, such as solutions, emulsions, suspensions, powders, pastes and granules, depending on the field of use.

These formulations can be prepared in a manner which is known per se, for example by mixing the active compound with an extender, which consists of a liquid solvent and/or solid carriers, if appropriate using surface-active agents, such as emulsifiers and/or dispersing agents, and, in the case of the use of water as the extender, organic solvents, such as alcohols, can also be used as auxiliaries if appropriate.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

Microbicidal agents in general contain the active compounds in an amount of 1 to 95%, preferably 10 to 75%.

The use concentrations of the active compounds according to the invention depend on the nature and occurrence of the microorganisms to be combated and on the composition of the material to be preserved. The optimum amount to be used can be determined by test series. The use concentrations are in general in the range from 0.001 to 5% by weight, preferably 0.05 to 1.0% by weight, based on the material to be preserved.

The active compounds according to the invention can also be present as a mixture with other known active compounds. The following active compounds may be mentioned as examples: benzyl alcohol mono(poly)-hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, organo-tin compounds, methylene bisthiocyanate, 2-thiocyanatomethylthiobenzothiazole and phenol derivatives, such as 2-phenylphenol, (2,2'-dihydroxy-5,5'-dichloro)diphenylmethane and 3-methyl-4-chlorophenol.

The preparation and use of the new cyanohydrin iodopropargyl ethers according to the invention can be seen from the following examples:

PREPARATION EXAMPLES

Example 1

Cyclohexenecarboxaldehyde-cyanohydrin iodopropargyl ether 32.5 g of KCN, 80 ml of $H_2O$, 160 ml of $CH_2Cl_2$ and 12.8 g of tetrabutylammonium bromide are taken and a mixture of 48 g of propargyl bromide and 44 g of 3-cyclohexenecarboxaldehyde is added dropwise, with stirring. Stirring is continued for 5 hours, the organic phase is separated off, the aqueous phase is extracted three times with 100 ml of $CH_2Cl_2$ each time and the organic solutions are combined, dried with $Na_2SO_4$ and concentrated. The resulting oil is distilled, boiling point 132°–6° C./15 mbar. Yield: 48 g of cyanohydrin propargyl ether.

43.8 g thereof are dissolved in 500 ml of methanol, the solution is cooled to 5° C. and 37 g of sodium methylate are added. 63.5 g of iodine are then added and the mixture is stirred at 0° to 5° C. for a further 2 hours. The mixture is poured into ice-water and the product is filtered off with suction. Yield 69 g of cyanohydrin iodopropargyl ether, melting point 62°–4° C., yellowish crystals.

The following compounds were prepared analogously:

| Example | R in formula (I) | Properties | IR |
| --- | --- | --- | --- |
| 2 | $CH_3CH_2$— | oil | 2185 cm$^{-1}$ |
| 3 | $(CH_3)_2CH$— | oil | 2190 cm$^{-1}$ |
| 4 | $CH_3CH_2CH_2$— | oil | 2187 cm$^{-1}$ |
| 5 | $(CH_3)_3C$— | melting point 36° C. | 2189 cm$^{-1}$ |
| 6 | $CH_3(CH_2)_3CH(C_2H_5)$— | oil | 2182 cm$^{-1}$ |

USE EXAMPLES

Example 7

To demonstrate the activity against fungi, the minimum inhibitory concentrations (MIC) of cyanohydrin iodoprpargyl ethers according to the invention and known iodopropargyl compounds were determined.

Active compounds according to the invention are added in concentraticns of 0.1 mg/l to 5,000 mg/l to an agar prepared from beer wort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentraion of active compound at which there is no growth at all of the species of microbe used; it is listed in the following table.

TABLE I

MICs [mg/l] for the action of various iodopropargyl ethers on fungi

| | Iodopropargyl ethers used | | | | |
|---|---|---|---|---|---|
| | Compounds according to the invention from Example | | | Compounds according to the prior art | |
| Test organisms | 1 | 2 | 3 | Compound A acc. to DEOS (German Patent Specification) 3,224,503 | Compound acc. to DEOS (German Patent Specification) 3,526,789 |
| *Alternaria tenuis* | 5 | 2 | 5 | 5 | 5 |
| *Aspergillus niger* | 0.5 | 2 | 1 | 5 | 5 |
| *Aureobasidium pullulans* | 5 | 5 | 2 | 10 | 5 |
| *Chaetomium globosum* | 5 | 3.5 | 10 | 10 | 20 |
| *Cladosporium cladosporioides* | 0.5 | | 1 | — | 5 |
| *Lentinus tigrinus* | 7.5 | 2 | 5 | 5 | 15 |
| *Penicillium glaucum* | 1 | 2 | 5 | 5 | 5 |
| *Polyporus versicolor* | | 1 | | 5 | — |
| *Sclerophoma pityophila* | 5 | 2 | 1.5 | 10 | 5 |

Example 8

Action against bacteria

Active compounds according to the invention are added in concentrations of 1 to 5,000 ppm to an agar containing broth as the nutrient medium. The nutrient medium is then infected with each of the test organisms listed in Table II and the infected medium is kept at 28° C. and 60 to 70% relative atmospheric humidity for 2 weeks. The MIC is the lowest concentration of active compound at which there is no growth at all of the species of microbe used. The MIC values are given in Table II.

TABLE II

MIC values in mg/l for action of the active compounds given below on bacteria.

| | MIC in mg/l of the active compound Compound of Example No. | | | | |
|---|---|---|---|---|---|
| Test organisms | 1 | 2 | 3 | 4 | 5 |
| *Escherichia coli* | 750 | 100 | 100 | 100 | 500 |
| *Staphylococcus aureus* | 50 | 100 | 100 | 100 | 200 |

Example 9

Action against slime organisms

The iodopropargyl ethers to be tested, dissolved in a little acetone, were in each case used in concentrations of 0.1 to 100 mg/l in Allens nutrient solution (Arch. Mikrobiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam in 4 l of sterile water. At the start of the test, the individual nutrient solutions are infected with slime organisms (about $10^6$ germs/ml) which have been isolated from spinning water circulations used in the preparation of polyamide. Nutrient solutions which contained the iodopropargyl ethers to be tested in at least the minimum inhibitory concentration (MIC) are still completely clear after culture for 3 weeks at room temperature; the slime formation which occurs after 3 to 4 days in nutrient solutions containing no active compound and which is caused by the substantial multiplication of the microbes, and the associated clouding are suppressed in these.

TABLE III

MIC value [mg/l] of the cyanohydrin iodopropargyl ethers according to the invention for action on slime organisms

| Cyanohydrin propargyl ether according to Example | MIC [mg/l] |
|---|---|
| 1 | 15 |
| 2 | 7.5 |
| 3 | 15 |
| 4 | 15 |

Example 10

Action against algae

A mixed culture of green, blue, brown and diatoms (*Stichococcus bacillaris* Naegeli, *Euglena gracilis* Klebs, *Chlorella pyrenoidosa* Chick, *Phormidium foveolarum* Gomont, *Oscillatoria geminata* Meneghini and *Phaeodactylum tricornutum* Bohlin) is added to Allens nutrient solution (Arch. Mikrobiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride in 4 l of sterile water, while bubbling through air. After 2 weeks, the nutrient solution is coloured a deep green-blue caused by the intensive growth of algae. The dying off of the algea after addition of the active compounds according to the invention is recognized by the decolorization of the nutrient solution.

TABLE IV

Algae-destroying concentrations [mg/l] of the cyanohydrin iodopropargyl ethers according to the invention

| Compound of Example No. | Destroying concentration [mg/l] |
|---|---|
| 1 | 100 |
| 2 | 100 |
| 3 | 100 |
| 4 | 100 |

Example 11

Fungicidal action in paints

The fungicidal action in paints is determined by testing the mould resistance of the paint films obtained from the paints.

Testing is carried out in accordance with report 219 of the Defense Standards Laboratories Maribyrnong-/Australia as follows:

The paint to be tested is brushed onto both sides of a suitable substrate.

To obtain results corresponding to those in practice, some of the test specimens are leached out with running water (24 hours; 20° C.) before the test for resistance to mould; some other test specimens are treated with a stream of warm fresh air (7 days; 40° C.).

The test specimens thus prepared are placed on an agar nutrient medium. The test specimen and nutrient medium are contaminated with fungal spores. Samples are taken after storage for 1 to 3 weeks at 29±1° C. and 80 to 90% relative humidity. The paint film has a persistent mould resistance if the test specimen remains free from fungi or reveals at most a slight attack at the edges.

Fungal spores of the following nine moulds which are known as destroyers of paint films or are frequently encountered on paint films are used for the contamination:

1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra* Corda An emulsion paint which is based on polyvinyl acetate and contains as a fungicide 0.5% by weight, based on the total solids content, of the cyanohydrin iodopropargyl ether described in Example 1 gives persistently mould-resistant paint films in the above test.

If, instead of the iodopropargyl ether described in Example 1, the iodopropargyl ether described in DE-OS (German Published Specification) 3,526,789 is used as the fungicide, mould-resistant paint films are still not obtained even at contents of 3% by weight.

What is claimed is:

1. A cyanohydrin iodopropargyl ether of the formula

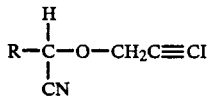

wherein
R is $C_2$-$C_{14}$-alkyl, $C_2$-$C_{14}$-alkenyl, $C_5$-$C_8$-cycloalkyl or -cycloalkenyl or $C_2$-$C_{14}$-alkyl, or $C_2$-$C_{14}$-alkenyl which is substituted by chlorine or bromine, or $C_5$-$C_8$-cycloalkyl and $C_5$-$C_8$-cycloalkenyl which is substituted by $C_1$-$C_4$-alkyl or chlorine or bromine.

2. The cyanohydrin iodopropargyl ether of claim 1, wherein
R is ethyl, propyl, cyclohexenyl or cyclohexenyl substituted by methyl.

3. A method of combating microorganisms comprising treating a material or adding to a material subject to microbial change or destructive a microbiocidally effective amount of a cyanohydrin iodopropargyl ether according to claim 1.

* * * * *